United States Patent [19]

Waddill et al.

[11] Patent Number: 4,665,191

[45] Date of Patent: May 12, 1987

[54] MANNICH CONDENSATES

[75] Inventors: Harold G. Waddill; George P. Speranza, both of Austin, Tex.

[73] Assignee: Texaco Inc., White Plains, N.Y.

[21] Appl. No.: 731,211

[22] Filed: May 6, 1985

[51] Int. Cl.$^4$ ............................................. C07D 233/64
[52] U.S. Cl. .................................... 548/336; 544/370; 548/337; 548/341
[58] Field of Search ......................... 548/341, 336, 337

[56] References Cited

U.S. PATENT DOCUMENTS 3,677,978  7/1972  Dowbenko et al. ............ 548/341 X
3,787,458  1/1974  Piasek et al. .................. 548/341 X

OTHER PUBLICATIONS

House, H., *Modern Synthetic Reactions*, 2nd Ed., Benjamin/Cummings, Menlo Park, Calif., 1972, p. 658.

Primary Examiner—Richard A. Schwartz
Attorney, Agent, or Firm—Jack H. Park; Kenneth R. Priem

[57] ABSTRACT

Mannich condensates prepared from an imidazole, formaldehyde and a polyalkylene polyamine are useful as curing agents for epoxy resins.

Preferably, a diamine is reacted with the imidazole and formaldehyde, as illustrated by the following formula:

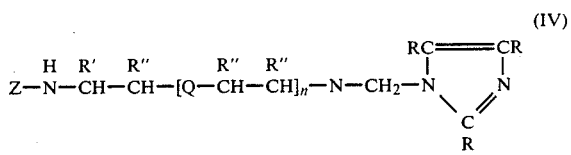

(IV)

wherein:
R represents hydrogen or a $C_1$–$C_4$ alkyl group;
At least one of R' and R" represents hydrogen and the other represents hydrogen or methyl;
n represents a number having an average value of 0 to about 100;
Q represents —O— or —NH—; and
Z represents H or

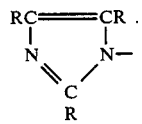

5 Claims, No Drawings

MANNICH CONDENSATES

BACKGROUND OF THE INVENTION

1. Field of Invention

This invention relates to Mannich condensates prepared from an imidazole, formaldehyde and a polyalkylene polyamine, as hereafter defined. The Mannich condensates are useful, for example, as curing agents for epoxy resins.

More particularly, this invention relates to Mannich condensates prepared from starting materials including an imidazole and a polyalkylene polyamine. The imidazole and the polyalkylene polyamine are reacted with formaldehyde under Mannich condensation reaction conditions to provide the desired reaction product.

In accordance with the preferred embodiment of the present invention the polyamine that is reacted with the imidazole is a diamine and, in this situation, the invention may be illustrated by the following formula:

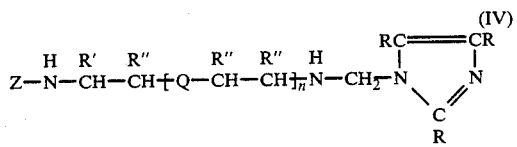 (IV)

Wherein:
R represents hydrogen or a $C_1$-$C_4$ alkyl group;
At least one of R' and R" represents hydrogen and the other represents hydrogen or methyl;
n represents a number having an average value of 0 to about 100;
Q represents —O— or —NH—; and
Z represents H or

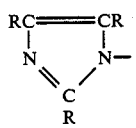

2. Prior Art

The Mannich reaction is a well known reaction which has been extensively reviewed in the literature. See for example, "The Mannich Reaction", *Org. Reactions* 1, 303 (1942) and "Advances in the Chemistry of Mannich Bases", *Methods in Synthetic Organic Chemistry-Synthesis*, Academic Press, pgs. 703–775, 1973.

Shimp U.S. Pat. No. 4,417,010 is directed to a liquid curing agent for polyepoxides having terminal epoxide groups which is a liquid blend of a monoimidazole compound and an aliphatic polyol.

Kaufman U.S. Pat. No. 4,420,605 discloses a coating composition comprising a 1,2-epoxy resin, a modified imidazole catalyst and a polyfunctional reactant such as a polyhydric phenol, a polycarboxylic acid or dicyandiamide.

SUMMARY OF INVENTION

It has been surprisingly discovered in accordance with the present invention that a new class of Mannich condensates having utility as epoxy resin curing agents can be provided when an imidazole feedstock is reacted with a polyalkylene polyamine feedstock and formaldehyde under Mannich reaction conditions.

STARTING MATERIALS

The Formaldehyde

Formaldehyde may be employed in any of its conventional forms. Thus it may be, and preferably is, used in the form of an aqueous solution of formaldehyde such as "formalin", and may also be used in "inhibited" methanol solution, as paraformaldehyde, or as trioxane.

The Imidazole Starting Material

The imidazoles to be used as starting materials are imidazoles having the following formula:

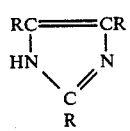 (I)

Wherein R represents H or a $C_1$ to $C_4$ alkyl group.

Representative compounds having this structure are imidazole and compounds such as 2-methyl imidazole, 2-ethyl-4-methyl imidazole, 4-methyl imidazole, 2-ethyl imidazole, 4-ethyl imidazole and the corresponding propyl and butyl analogs.

The Polyamine Starting Materials

The polyalkylene polyamines to be used as starting materials in accordance with the present invention are those having the following formula:

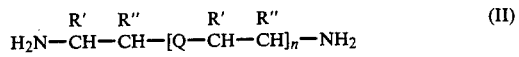 (II)

Wherein:
Q represents —O— or —NH—,
n represents a number having an average value of 0 to about 100, and
at least one of R' and R" represents hydrogen and the other represents hydrogen or methyl.

It will be seen from the above that the foregoing formula includes ethylene diamine, propylene diamine, polyethylene polyamines, polypropylene polyamines, polyoxyethylene polyamines and polyoxypropylene polyamines.

As an example, a polyethylenepolyamine may be used such as one having the following formula:

 (III)

Wherein n has a value of about 2 to about 10.

As another example, the amine may be a polyoxypropylene diamine having the formula:

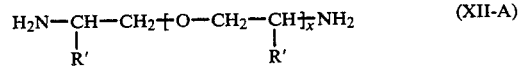 (XII-A)

Wherein R' independently represents hydrogen or methyl.

Examples of polyoxyalkylenediamines of this formula which are useful in accordance with the present invention are those wherein x has a value of 3 to about 40 such as those compounds known as Jeffamine D (Formula XII) series of compounds available from Texaco Chemical Company.

Another example of a suitable amine to be used in accordance with the present invention is a polyoxyethylenediamine such as one having the formula:

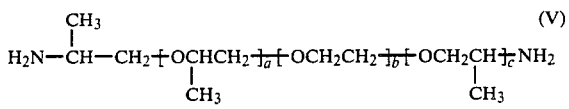

Examples of suitable polyoxyethylenediamines having this formula are given in the following table:

TABLE II

| Product | Approximate Value | |
|---|---|---|
| | b | a + c |
| JEFFAMINE ED-600 | 8.5 | 2.5 |
| JEFFAMINE ED-900 | 15.5 | 2.5 |
| JEFFAMINE ED-2001 | 40.5 | 2.5 |
| JEFFAMINE ED-4000 | 86.0 | 2.5 |

Still another example of an amine to be used in accordance with the present invention is a polyoxypropylenetriamine having the formula:

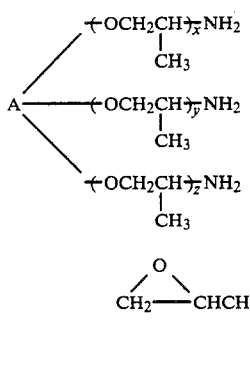

Wherein the sum of x+y+z is about 4 to 100.

Examples of suitable products having this formula include:

TABLE III

| Product | Initiator (A) | Approx. MW | Moles PO |
|---|---|---|---|
| T-403 | TMP | 400 | 5-6 |
| T-5000 | Glycerine | 5000 | 85 |

Preparation of the Mannich Condensate

The relative quantities of imidazole, formaldehyde and amine will be determined by the nature of the desired final product. If a monosubstituted Mannich condensate is desired, the imidazole starting material, the amine starting material and the formaldehyde should be used in approximately equimolar amounts. As another example, if a bis Mannich condensate is desired, then about 2 mole equivalents of formaldehyde and about one mole equivalent of polyamine should be used per 2 moles of imidazole starting material.

The reaction is preferably conducted at atmospheric pressure although subatmospheric pressures and/or superatmospheric pressures may be used, if desired.

The reaction is normally conducted at a temperature within the range of about 80° to about 120° when the amine has an average molecular weight of about 500 or less.

However, when higher molecular weight amines are used, it is necessary to use higher temperatures and/or pressures, such as temperatures within the range of about 100° to about 150° C. and pressures within the range of about 1 atmosphere to about 50 atmospheres.

UTILITY OF MANNICH CONDENSATES AS EPOXY CURING AGENTS

A particular utility for which the Mannich condensates of the present invention are well suited is found when the Mannich condensates are used as curing agents for 1,2-epoxy resins.

It is known to use amines such as aliphatic or aromatic amines for curing 1,2-epoxy resins as shown, for example, by Waddill U.S. Pat. No. 4,139,524 and Marquis et al. U.S. Pat. No. 4,162,358. See also, the textbook "Handbook of Epoxy Resins" by H. Lee and K. Neville, McGraw-Hill Book Company, 1967.

Generally the vicinal epoxide compositions that can be cured using the curing agents of this invention are organic materials having an average of more than one reactive 1,2-epoxide group. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, halogenated phenyl groups and the like.

The most widely used epoxy resins are diglycidyl ethers of bisphenol A:

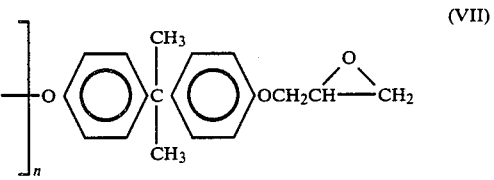

where n equals an integer of up to about 10 to 20.

However, these epoxides are representative of the broader class of epoxide compounds that are useful in making epoxy resins.

A widely used class of polyepoxides that can be cured according to the practice of the present invention includes the resinous epoxy polyethers obtained by reacting an epihalohydrin, such as epichlorohydrin, and the like, with either a polyhydric phenol or a polyhydric alcohol. An illustrative, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'-dihydroxydiphenylmethylpropylmethane, 2,3'-dihydroxydiphenylethylphenylmethane, 4,4'-dihydroxydiphenylmethane, 4,4'-dihydroxydiphenylbutylphenylmethane, 2,2'-dihydroxydiphenylditolylmethane, 4,4'-dihydroxydiphenyltolylmethyl-methane and the like. Other polyhydric phenols which may also be co-reacted with an epihalohydrin to provide these epoxy polyethers are such compounds as resorcinol, hydroquinone, substituted hydroquinones, e.g., tert-butylhydroquinones, and the like.

Among the polyhydric alcohols that can be co-reacted with an epihalohydrin to provide the resinous epoxy polyethers are such compounds as ethylene glycol, propylene glycol, butylene glycols, pentane diols, bis(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, such as 2,2'- 3,3'-tetrahydroxydipropylsulfide and the like, mercapto alcohols such as α-monothioglycerol, α,α'-dithioglycerol, and the like, polyhydric alcohol partial esters, such as monostearin, pentaerythritol monoacetate, and the like, and halogenated polyhydric alcohols such as the monochlorohydrins of glycerol, sorbitol, pentaerythritol and the like.

Another class of polymeric polyepoxides that can be cured by means of the above-described curing agents includes the epoxy novolac resins obtained by reacting, preferably, in the presence of a basic catalyst, e.g., sodium or potassium hydroxide, an epihalohydrin, such as epichlorohydrin, with the resinous condensate of an aldehyde, e.g., formaldehyde, and either a monohydric phenol, e.g., phenol itself, or a polyhydric phenol. Further details concerning the nature and preparation of these epoxy novolac resins can be obtained in Lee, H. and Neville, K. "Handbook of Epoxy Resins".

It will be appreciated by those skilled in the art that the polyepoxide compositions that can be cured according to the practice of the present invention are not limited to the above described polyepoxides, but that these polyepoxides are to be considered merely as being representative of the class of polyepoxides as a whole.

The amount of curing agent that is employed in curing polyepoxide compositions will depend on the amine equivalent weight of the curing agent employed. The total number of equivalents of amine group is preferably from about 0.8 to about 1.2 times the number of epoxide equivalents present in the curable epoxy resin composition with a stoichiometric amount being most preferred.

Various conventionally employed additives can be admixed with these polyepoxide-containing compositions prior to final cure. For example, in certain instances it may be desired to add minor amounts of other co-catalysts, or hardeners, along with the curing agent system herein described. Conventional pigments, dyes, fillers, flame retarding agents and other compatible natural and synthetic resins can also be added. Furthermore, known solvents for the polyepoxide materials such as acetone, methyl ethyl ketone, toluene, benzene, xylene, dioxane, methyl isobutyl ketone, dimethylformamide, ethylene glycol monoethyl ether acetate, and the like, can be used if desired, or where necessary.

WORKING EXAMPLES

Reaction of Amines, Formaldehyde and Imidazoles

Reaction of Jeffamine D-400 amine with formalin and imidazole is illustrated below.

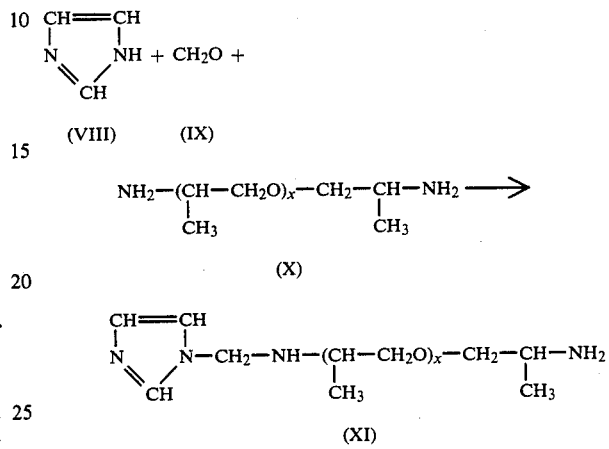

x = 5.6

To a 250 ml 3-necked flask equipped with a stirrer, thermometer and dropping funnel was added 6.8 g of imidazole (0.1 mole) and 40 g of Jeffamine D-400 amine (0.1 mole). The mixture was heated to 90° C. to dissolve the imidazole. The mixture was cooled to 29° C. and 8.1 g of 37% formalin was added portionwise keeping the temperature below 50° C. The contents were held at 45°–50° C. for 30 minutes and then heated at 100° C. and 15 mm. pressure for two hours to remove water. The product was a fluid light colored liquid.

The procedure described above was used to prepare the products described in Table I. In most cases the reactants were heated at 110° C. for two hours prior to going under vacuum. The reactions are believed to take place at the 1-H position of imidazole and the C-alkyl substituted imidazoles. A model compound was prepared from imidazole, formaldehyde and methoxypropyl amine. Analysis by NMR and IR indicated substitution at the 1-position.

Summary of reaction data is shown in Table I, enclosed.

Example 1
Glass Transition Temperatures (Tg) of
Amine.Imidazole.Formaldehyde Condensates

| Condensate Composition | Molar* Ratio of Condensate | Notebook Number | Optimum Tg, °C. | Curative Conc., phr. at Opt. Tg |
|---|---|---|---|---|
| Jeffamine D400.Imidazole.CH$_2$O | 1:1:1 | 5728-16 | 128.6 | 16 |
| Jeffamine D400.2MeImidazole.CH$_2$O | 1:1:1 | 5728-25 | 143.0 | 16 |
| Jeffamine D400.Imidazole.CH$_2$O | 1:2:2 | 5728-27 | 149.8 | 12 |
| Jeffamine D400.2MeImidazole.CH$_2$O | 1:2:2 | 5728-26 | 172.7 | 11 |
| Jeffamine D400.1MeImidazole.CH$_2$O | 1:1:1 | 5728-30 | 126.4 | 14 |
| Diethylenetriamine.Imidazole.CH$_2$O | 1:1:1 | 5728-50 | 154.3 | 6 |
| N—Aminoethylpiperazine.Imidazole.CH$_2$O | 1:1:1 | 5728-51 | 154.3 | 8 |
| Dipropylenetriamine.Imidazole.CH$_2$O | 1:1:1 | 5728-59 | 160.4 | 6 |
| Jeffamine D230.Imidazole.CH$_2$O | 1:1:1 | 5728-58 | 142.0 | 12 |
| Dipropylenetriamine.2MeImidazole.CH$_2$O | 1:1:1 | 5906-5 | 182.0 | 6 |
| Jeffamine D400.2Et4MeImidazole.CH$_2$O | 1:1:1 | 5728-29 | 132.6 | 19 |
| Dipropylenetriamine.2MeImidazole.CH$_2$O | 1:2:2 | 5906-7 | 184.3 | 6 |
| Isophoronediamine.2MeImidazole.CH$_2$O* | 1:1:1 | 5906-14 | 193.1 | 10 |

Example 1
Glass Transition Temperatures (Tg) of Amine.Imidazole.Formaldehyde Condensates

| Condensate Composition | Molar Ratio of Condensate | Notebook Number | Optimum Tg, °C. | Curative Conc., phr. at Opt. Tg |
|---|---|---|---|---|
| 1,3-Diaminocyclohexane.2MeImidazole.CH$_2$O* | 1:1:1 | 5906-15 | 185.6 | 8 |

*1,3-Diaminocyclohexane and isophoronediamine are cycloaliphatic (e.g., cyclohexyl) diamines.

Example 1A
Glass Transition Temperatures (Tg): Comparison of Tg of Blends and Condensates

| Curative Composition | Optimum Tg, °C. | Curative Conc., Phr. at Opt. Tg. |
|---|---|---|
| Jeffamine D400.Imidazole Blend (8.6-1.4 pbw mixture) | 124.0 | 10 |
| Jeffamine D400.Imidazole.CH$_2$O Cond. (5728-16) | 128.6 | 16 |
| Dipropylenetriamine.2MeImidazole Blend (6.1-3.9 pbw mixture) | 175.5 | 5 |
| DPTA.2MeImidazole.CH$_2$O Cond. (5906-05) | 182.0 | 6 |
| Diethylenetriamine.Imidazole Blend (6.3-3.7 pbw mixture) | 156.4 | 4 |
| DETA.Imidazole.CH$_2$O Cond. (5906-21) | 162.6 | 6 |

Example 2
Comparison of Properties: Curing with Jeffamine D-400 Imidazole Formaldehyde Condensate and Related Product Blend

| | 5882-44A | 5882-77B |
|---|---|---|
| Formulation | | |
| Liquid epoxy resin (EEW ~185) | 100 | 100 |
| Jeffamine D400.Imidazole.CH$_2$O Condensate (5728-27) | 12 | — |
| Jeffamine D-400 | — | 5.2 |
| Imidazole | — | 1.8 |
| Exothermic Properties | | |
| Brookfield Viscosity, cps., ~25° C. | 25000 | 9000 |
| Gel time, minutes (200 g mass) | 2 | 3 |
| Peak exothermic temp., °C. | 30.3 | 29.0 |
| Time to peak temp., minutes | ~540 | ~220 |
| Physical Properties:[1] | | |
| Izod impact strength, ft-lbs/in. | 0.12 | 0.11 |
| Tensile strength, psi | 7000 | 6800 |
| Tensile modulus, psi | 351000 | 344000 |
| Elongation at break, % | 2.9 | 2.9 |
| Flexural strength, psi | 12000 | 11100 |
| Flexural modulus, psi | 388000 | 368000 |
| HDT, °C., 264 psi/66 psi | 136/150 | 140/152 |
| Shore D hardness, 0-10 sec. | 85-83 | 81-79 |
| Compression strength, | | |
| to yield, psi | — | — |
| to failure, psi | 36600 | 24650 |
| % weight gain, | | |
| 24 hr. water boil | 1.7 | 1.5 |
| 3 hr. acetone boil | 0.2 | 0.3 |

[1]Cured 2 hours, 100° C., 3 hours, 150° C.
[2]Time to viscosity of:
50,000 cps - 210 minutes
100,000 cps - ~350 minutes
Not gelled after 24 hours, ~25° C.
[3]Time to viscosity of
10,000 cps ~100 minutes
20,000 cps ~230 minutes
30,000 cps ~300 minutes
40,000 cps 362 minutes
50,000 cps ~400 minutes

Example 3
Comparison of Properties: Curing with Dipropylenetriamine (DPTA).Imidazole. Formaldehyde Condensate and Related Blend

| | 5882-46A | 5882-77C |
|---|---|---|
| Formulation | | |
| Liquid epoxy resin (EEW ~185) | 100 | 100 |
| DPTA Imidazole.CH$_2$O Condensate (5728-59) | 6 | — |
| DPTA (5674-16-8) | — | 3.2 |
| Imidazole | — | 1.8 |
| Exothermic Properties | | |
| Brookfield Viscosity, cps., ~25° C. | 14000 | 7200 |
| Gel time, minutes (200 g mass) | 2 | ~160 |
| Peak exothermic temp., °C. | 40.0 | 45.1 |
| Time to peak temp., minutes | ~90 | 140 |
| Physical Properties:[1] | | |
| Izod impact strength, ft-lbs/in. | 0.15 | 0.15 |
| Tensile strength, psi | 7000 | 7400 |
| Tensile modulus, psi | 375500 | 378000 |
| Elongation at break, % | 2.2 | 2.8 |
| Flexural strength, psi | 12350 | 13300 |
| Flexural modulus, psi | 388000 | 394000 |
| HDT, °C., 264 psi/66 psi | 149/162 | 149/159 |
| Shore D hardness, 0-10 sec. | 80-78 | 82-80 |
| Compression strength, | | |
| to yield, psi | — | — |
| to failure, psi | | 24300 |
| % weight gain, | | |
| 24 hr. water boil | 2.2 | 1.6 |
| 3 hr. acetone boil | 0.16 | 0.22 |

[1]Cured 2 hours, 100° C., 3 hours, 150° C.
[2]Viscosity reached
20,000 cps after ~40 minutes
50,000 cps after ~130 minutes
90,000 cps after ~150 minutes

Example 4
Comparison of Properties: Curing with Diethylenetriamine (DETA).Imidazole. Formaldehyde Condensate and Related Blend

| | 5882-39A | 5882-77A |
|---|---|---|
| Formulation | | |
| Liquid epoxy resin (EEW ~185) | 100 | 100 |
| DETA.Imidazole.CH$_2$O Condensate (5728-80) | 6 | — |
| DETA | — | 2.5 |
| Imidazole | — | 1.5 |
| Exothermic Properties | | |
| Brookfield Viscosity, cps., ~25° C. | 13500 | 6000 |
| Gel time, minutes (200 g mass) | ~65 | 60.8 |
| Peak exothermic temp., °C. | 163.0 | 228.0 |
| Time to peak temp., minutes | ~155 | 93.0 |
| Physical Properties:[1] | | |
| Izod impact strength, ft-lbs/in. | 0.14 | 0.15 |
| Tensile strength, psi | 6300 | 7400 |
| Tensile modulus, psi | 390000 | 378000 |
| Elongation at break, % | 1.9 | 2.8 |
| Flexural strength, psi | 11450 | 13300 |
| Flexural modulus, psi | 432500 | 394000 |
| HDT, °C., 264 psi/66 psi | 153/166 | 149/159 |
| Shore D hardness, 0-10 sec. | 86-84 | 82-80 |
| Compression strength, | | |

-continued

Example 4
Comparison of Properties: Curing with
Diethylenetriamine (DETA).Imidazole.
Formaldehyde Condensate and Related Blend

|  | 5882-39A | 5882-77A |
|---|---|---|
| to yield, psi | — | — |
| to failure, psi | 21800 | 24300 |
| % weight gain, |  |  |
| 24 hr. water boil | 1.9 | 1.8 |
| 3 hr. acetone boil | 0.06 | 0.12 |

[1] Cured 2 hours, 100° C., 3 hours, 150° C.

TABLE I

REACTIONS OF AMINES, FORMALDEHYDE AND IMIDAZOLES

| Run No. | Amine | Grams Moles | Formaldehyde (37%) | Grams Moles | Imidazole | Grams Moles | Product Wt. (gr) |
|---|---|---|---|---|---|---|---|
| 5728-16 | Jeffamine D400 | 40 gr. 0.1 m | Formalin | 8.1 gr 0.1 m | Imidazole | 6.8 gr 0.1 m | 47.4 |
| 5728-21 | Jeffamine T403 | 27.9 0.1 | Formalin | 8.1 0.1 | Imidazole | 6.8 0.1 | 35.8 |
| 5728-22 | Jeffamine D2000 | 200.0 | Formalin | 8.1 0.1 | Imidazole | 6.8 0.1 | 207.1 |
| 5728-25 | Jeffamine D400 | 200.0 | Formalin | 40.5 0.5 | 2-Methyl imidazole | 41.0 0.5 | 246.1 |
| 5728-26 | Jeffamine D400 | 200 | Formalin | 81.0 1.0 | 2-Methyl imidazole | 82.0 1.0 | 293.5 |
| 5728-27 | Jeffamine D400 | 200 | Formalin | 81.0 1.0 | Imidazole | 68.0 0.85 | 276.2 |
| 5728-29 | Jeffamine D400 | 134 | Formalin | 27.0 0.33 | 2-Et—4-Me imidazole | 37.0 0.33 | 173.8 |
| 5728-30 | Jeffamine D400 | 200 | Formalin | 41.0 0.5 | N—methyl imidazole | 41.0 | 238.2 |
| 5728-48 | Jeffamine ED900 | 90 | Formalin | 8.1 0.1 | Imidazole | 6.8 0.1 | 97.4 |
| 5728-49 | Jeffamine T5000 | 500.0 | Formalin | 8.1 0.1 | Imidazole | 6.8 0.1 | 506.7 |
| 5728-50 | Diethylene-triamine | 30.9 | Formalin | 24.3 0.3 | Imidazole | 18.3 | 51.1 |
| 5728-51 | Aminoethyl-piperazine | 38.7 | Formalin | 24.3 0.3 | Imidazole | 18.3 | 59.9 |
| 5728-54 | Jeffamine D230 | 46.0 0.2 | Formalin | 16.2 0.2 | Imidazole | 13.6 0.2 | 59.1 |
| 5728-58 | Jeffamine D230 | 46.0 0.2 | Formalin | 16.2 0.2 | Imidazole | 13.6 0.2 | 61.2 |
| 5728-59 | Dipropylene-triamine | 25.4 0.2 | Formalin | 16.2 0.2 | Imidazole | 13.8 0.2 | 39.9 |
| 5728-73 | Diethylene-triamine | 92.7 | Formalin | 72.9 | Imidazole | 54.9 | 154.6 |
| 5728-74 | Aminoethyl-piperazine | 154.8 | Formalin | 97.2 | Imidazole | 53.2 | 217.6 |
| 5728-80 | Diethylene-triamine | 154.5 | Formalin | 121.5 0.33 | Imidazole | 92.5 0.33 | 229.0 |
| 5728-81 | Aminoethyl-piperazine | 193.5 | Formalin | 121.5 | Imidazole | 91.5 | 226.8 |
| 5728-82 | Ethylenediamine | 24.0 0.4 | Formalin | 32.4 0.4 | Imidazole | 27.2 0.4 | 45.2 |
| 5728-83 | 1,2-propylene diamine | 30.8 0.4 | Formalin | 32.4 0.4 | Imidazole | 27.2 0.4 | 40.9 |
| 5728-84 | Aminoethyl-piperazine | 193.5 | Formalin | 121.5 | Imidazole | 91.5 | 299.0 |
| 5728-86 | Jeffamine D400 | 120.0 0.3 | Formalin | 24.3 0.3 | Benzimid-azole | 35.5 0.3 | 157.8 |
| 5728-87 | Jeffamine D400 | 120.0 0.3 | Formalin | 48.6 0.6 | Benzimid-azole | 71.0 0.6 | 196.8 |
| 5728-93 | Methoxypropyl-amine | 18.2 0.2 | Formalin | 16.2 0.2 | Imidazole | 13.6 0.2 | 22.9 |
| 5728-96 | Methoxypropyl-amine | 27.3 0.3 | Formalin | 24.3 0.3 | Benzimid-azole | 35.5 0.3 | 60.3 |
| 5906-4 (5728-16 Scale-up) | Jeffamine D400 | 400.0 1.0 | Formalin | 81.0 1.0 | Imidazole | 68.0 1.0 | 477.9 |
| 5906-5 | Dipropylene-triamine | 126 1.0 | Formalin | 81.0 1.0 | 2-methyl imidazole | 82.0 1.0 | 215.4 |

Product Appearance 5728-16 Fluid light colored liquid
5728-21 Almost colorless viscous liquid
5728-22 Viscous light gold color at room temp.
5728-25 Clear yellow liquid
5728-26 Golden viscous liquid
5728-27 Very viscous gold-orange color at R.T.
5728-29 Clear golden liquid
5728-30 Clear light yellow liquid
5728-48 Clear light yellow liquid
5728-49 Viscous light gold color at R.T.
5728-50 Orange liquid
5728-51 Nonpourable liquid-light colored

TABLE I-continued
REACTIONS OF AMINES, FORMALDEHYDE AND IMIDAZOLES

| | |
|---|---|
| 5728-54 | Viscous black liquid |
| 5725-58 | Burnt orange fluid liquid |
| 5728-59 | Gold color slight viscous material |
| 5728-73 | Yellow viscous liquid |
| 5728-74 | Yellow, nonpourable liquid |
| 5728-80 | Orange viscous liquid |
| 5728-81 | Orange-yellow clear solid |
| 5728-82 | Orange solid at R.T. |
| 5728-83 | Sticky, gel-like orange liquid |
| 5728-84 | Nonpourable light yellow |
| 5728-86 | Slightly viscous dark brown at R.T. |
| 5728-87 | Very viscous dark brown at R.T. |
| 5728-93 | Clear golden solid |
| 5728-96 | Brown liquid-solid |
| 5906-4 | Yellow-gold liquid |
| 5906-5 | Yellow fluid liquid |

Jeffamine D-230 and D-400 are represented by the following structure:

$$H_2NCH(CH_3)CH_2 + OCH_2CH(CH_3)]_x NH_2 \quad (XII)$$

| JEFFAMINE | x (approx.) |
|---|---|
| D-400 | 5.6 |
| D-230 | 2.6 |

JEFFAMINE T-403 has the following structure:

$$\begin{array}{l} CH_2[OCH_2CH(CH_3)]_x NH_2 \\ | \\ CH_3CH_2CCH_2[OCH_2CH(CH_3)]_y NH_2 \\ | \\ CH_2[OCH_2CH(CH_3)]_z NH_2 \end{array} \quad (XIII)$$

$$x + y + z = 5.3$$

The formula for Jeffamine T-5000:

$$\begin{array}{l} \quad\quad\quad CH_3 \\ \quad\quad\quad | \\ CH_2C-[O-CH_2-CH]_x-NH_2 \\ | \quad\quad\quad CH_3 \\ | \quad\quad\quad | \\ CH_2C-[O-CH_2-CH]_y-NH_2 \\ | \quad\quad\quad CH_3 \\ | \quad\quad\quad | \\ CH_2C-[O-CH_2-CH]_z-NH_2 \end{array} \quad (XIV)$$

$$x + y + z = \sim 85$$

Amines such as JEFFAMINE-ED 900 may be generically represented by the formula:

$$\begin{array}{c} CH_3 \quad\quad CH_3 \quad\quad\quad\quad\quad CH_3 \\ | \quad\quad\quad | \quad\quad\quad\quad\quad\quad | \\ H_2NCCH_2(OCHCH_2)_{ax}(OCH_2CH_2)_b(OCH_2CH)_c NH_2 \\ | \\ H \end{array} \quad (V)$$

wherein a plus c equal about 3.5 and b equals about 13 to 46.

Dipropylene triamine refers to the formula:

$$\begin{array}{c} NH_2-CH_2-CH-NH-CH_2-CH-NH_2 \\ \quad\quad\quad\quad | \quad\quad\quad\quad\quad | \\ \quad\quad\quad\quad CH_3 \quad\quad\quad\quad CH_3 \end{array}$$

It will be understood that the foregoing examples are given by way of illustration only and not by way of limitation and that the scope of the present invention is defined solely by the appended claims.

What is claimed is:

1. A Mannich condensate having formula IV or V, as follows:

$$\begin{array}{c} \quad R' \quad R'' \quad\quad R'' \quad R'' \quad\quad\quad RC\!=\!\!=\!\!CR \\ H \quad | \quad\quad | \quad\quad\quad | \quad\quad | \quad\quad H \quad\quad\quad | \quad\quad\quad | \\ Z-N-CH-CH-[Q-CH-CH]_n-N-CH_2-N \quad\quad N \\ \quad\quad\quad\quad\quad\quad\quad\quad\quad\quad\quad\quad\quad\quad\quad\quad\quad\quad\quad\quad\quad\quad\quad\backslash\;/ \\ \quad\quad\quad\quad\quad\quad\quad\quad\quad\quad\quad\quad\quad\quad\quad\quad\quad\quad\quad\quad\quad\quad\quad\quad C \\ \quad\quad\quad\quad\quad\quad\quad\quad\quad\quad\quad\quad\quad\quad\quad\quad\quad\quad\quad\quad\quad\quad\quad\quad R \end{array} \quad (IV)$$

Wherein
Q represents —O— or —NH—,
n represents a number having an average value of 0 to about 100,
R represents H or a $C_1$ to $C_4$ alkyl group,
at least one of R' and R" represents hydrogen and the other represents hydrogen or methyl, and
Z represents H or $$\begin{array}{c} RC\!=\!\!=\!\!CR \\ | \quad\quad\quad | \\ N \quad\quad N- \\ \backslash\;/ \\ C \\ | \\ R \end{array} \quad (V)$$

or:

$$\begin{array}{c} \quad\quad\quad\quad\quad\quad CH_3 \\ \quad\quad\quad\quad\quad\quad | \\ \quad\quad[O-CH_2-CH]_x-NHZ' \\ / \\ \quad\quad\quad\quad\quad\quad CH_3 \\ \quad\quad\quad\quad\quad\quad | \\ A-\!\!-\!\!-[O-CH_2-CH]_x-NHZ'' \\ \backslash \\ \quad\quad\quad\quad\quad\quad CH_3 \\ \quad\quad\quad\quad\quad\quad | \\ \quad\quad[O-CH_2-CH]_x-NHZ''' \end{array}$$

Wherein:
A represents a trifunctional initiator selected from the group consisting of glycerine and trimethylolpropane,
x, y and z represents number, and the sum of x+y+z=4 to about 100, and
Z' represents H or $$\begin{array}{c} RC\!=\!\!=\!\!CR \\ | \quad\quad\quad | \\ N \quad\quad N- \\ \backslash\;/ \\ C \\ | \\ R \end{array}$$

and

Z″ and Z‴ represent H or
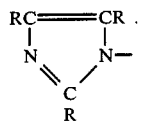
2. A Mannich condensate as in claim 1 of formula IV.
3. A Mannich condensate as in claim 2 wherein Q represents —O—.
4. A Mannich condensate as in claim 2 wherein Q represents —NH—.
5. A condensate as in claim 1 of formula V.
* * * * *